United States Patent [19]

Berg et al.

[11] Patent Number: 5,674,208
[45] Date of Patent: Oct. 7, 1997

[54] THIN-WALLED CATHETER

[75] Inventors: Todd A. Berg, White Bear Lake; Henry Pepin, Loretto; Brian Scovil, New Hope, all of Minn.

[73] Assignee: SciMed Life Systems, Inc., Maple Grove, Minn.

[21] Appl. No.: 489,001

[22] Filed: Jun. 8, 1995

Related U.S. Application Data

[63] Continuation of Ser. No. 108,973, Aug. 18, 1993, abandoned.

[51] Int. Cl.$^6$ ............................................. A61M 25/00
[52] U.S. Cl. ............................................................ 604/282
[58] Field of Search ................................. 604/282, 264, 604/280

[56] References Cited

U.S. PATENT DOCUMENTS

| | | | |
|---|---|---|---|
| 3,485,234 | 12/1969 | Stevens | 128/2 |
| 3,612,058 | 10/1971 | Ackerman | 128/348 |
| 4,516,972 | 5/1985 | Samson | 604/252 |
| 4,705,511 | 11/1987 | Kocak | 604/282 |
| 4,817,613 | 4/1989 | Jaraczewski | 604/282 |
| 4,842,590 | 6/1989 | Tanabe et al. | 604/282 |
| 4,898,591 | 2/1990 | Jang et al. | 604/282 |
| 5,057,092 | 10/1991 | Webster | 604/282 |
| 5,069,674 | 12/1991 | Fearnot et al. | 604/282 |
| 5,190,520 | 3/1993 | Fenton, Jr. et al. | 604/282 |
| 5,217,440 | 6/1993 | Frassica | 604/282 |
| 5,221,270 | 6/1993 | Parker | 604/282 |
| 5,221,372 | 6/1993 | Olson | 148/326 |
| 5,254,107 | 10/1993 | Soltesz | 604/282 |
| 5,306,252 | 4/1994 | Yutori et al. | 604/164 |

FOREIGN PATENT DOCUMENTS

| | | | |
|---|---|---|---|
| 0 277 366/A1 | 6/1987 | European Pat. Off. | |
| 473045 | 3/1992 | European Pat. Off. | 604/282 |
| 2404656 | 8/1975 | Germany | 604/282 |

OTHER PUBLICATIONS

Kolobow et al., "A New Thin-walled Nonkinking Catheter for Peripheral Vascular Cannulation", Surgery, vol. 68, No. 4, pp. 625–626. Oct. 1970.

*Primary Examiner*—Todd E. Manahan
*Attorney, Agent, or Firm*—Nawrocki, Rooney & Sivertson, P.A.

[57] ABSTRACT

An intravascular flexible catheter of the type having an inner tubular member defining a lumen, an outer tubular member surrounding the inner tubular member, and a metallic support member situated between the tubular members to provide rigidity to the flexible catheter. In the preferred embodiment the support member comprises a stainless steel wire braid which has been tempered or hardened to give it a significantly higher tensile strength than the prior art annealing process. This higher tensile strength affords significantly greater kink resistance to the flexible catheter as the lumen size is increased and the wall thickness is decreased.

2 Claims, 3 Drawing Sheets

THIN-WALLED CATHETER

CROSS REFERENCE TO CO-PENDING APPLICATIONS

This application is a continuation of U.S. patent application Ser. No. 08/108,973, filed Aug. 18, 1993, entitled "Thin-Walled Catheter" now abandoned.

BACKGROUND OF THE INVENTION

1. Field of the Invention

The present invention generally relates to the field of intravascular medicine and more particularly to the field of catheters such as guide catheters used for the placement of medicines and medical devices within the body.

2. Description of the Prior Art

The use of intravascular catheters for treatment of the body is well known in the field of medicine. The need for a choice of catheter sizes and types has grown rapidly as the techniques for their use have been greatly improved and the types of medical uses have rapidly expanded.

Prior art catheters often comprise a pair of congruent tubes, the inner one defining a lumen. A hub is connected at the proximal end of the tubes which in addition to providing access to the lumen for fluids and the like, is often used to provide torques and other necessary pressures to the tubes during their placement within the body. A tip of a selected design is placed at the distal end of the tubes. Flexibility is an essential part of the catheter so that it may be successfully torqued, pushed and pulled on its way through the vascular passage to the desired site in the body. For control of the catheter and to prevent its kinking from excessive flexing a certain amount of rigidity is required. The prior art catheters often meet this need for rigidity by adding a support member between the two tubes. This support member may comprise a braid of metal wire wrapped around the inner tube, and often imbedded within the outer tube.

As specific examples of the type of prior art catheters described above, note U.S. Pat. No. 3,485,234, issued Dec. 23, 1969, to R. C. Stevens; U.S. Pat. No. 4,516,972, issued May 14, 1985, to W. J. Samson; U.S. Pat. No. 4,898,591, issued Feb. 6, 1990, to Jang et al; and, European Patent Application, Publication No. 0 277 366/A1, Priority Jun. 1, 1987, by Bruce H. Wand et al. Each of these references teaches, in general, the prior art type of catheter discussed above.

One problem that has arisen is that as it becomes desirable to increase the diameter of the catheter lumen, it also becomes desirable to decrease the thickness of the walls of the tubes that form the catheter. However, it has been found that in thin-walled catheters it is more difficult to prevent the kinking of the catheter. This negative effect on flexibility is a problem for practitioners of the catheter art.

The above cited reference to Jang et al mentions in passing that a higher tensile strength for a support member is desirable. The references to Samson and Wand et al teach the use of a support member comprised of a braided ribbon made of a material such as Dupont Kevlar yarn, a non-metallic Aramid fiber. Kevlar has a tensile strength up to 400 Kpsi but has a Modulus of Elasticity less than 18,000,000 psi.

SUMMARY OF THE INVENTION

The present invention overcomes the disadvantages found in the prior art by providing an improved metallic support member that has a greater tensile strength and a greater Modulus of Elasticity than non-metallic support materials and therefore can offer an increase in the rigidity required to prevent kinking without sacrificing the needed flexibility. The increased tensile strength of the present invention is primarily achieved through the tempering or hardening of the metal used for the support member. In the prior art, the support member, such as a stainless steel braid, was annealed, thus resulting in a comparatively low tensile strength.

In the preferred embodiment of this invention the support member comprises a braid made of tempered stainless steel wires. A fully hardened metal wire is preferred, such as #304 stainless steel which will yield a tensile strength in the range of 300 to 475 kilopounds per square inch (kpsi) and which has a Modulus of elasticity ranging from 28,000,000 psi fully hardened to 26,000,000 not fully hardened. Other types of stainless steel can be used, including those having lower tensile strength. It has been found that tensile strengths as low as 200 kpsi offer advantageous kink performance.

Also, in the preferred embodiment of this invention, the preferred diameter of the braiding wire has been found to be 0.002 inches. However, it should also be noted that other diameters can be successfully utilized, such as in the range of 0.00075 to 0.0035 inches, dependent on the dimensions of the catheter thin wall.

In the preferred embodiment of this invention it has further been found that the preferred braid construction is 16 strands of tubular braid, with a braid density of 40 crosses per inch (pic). Other combinations of braid strands and pic densities have also been found to be useful.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
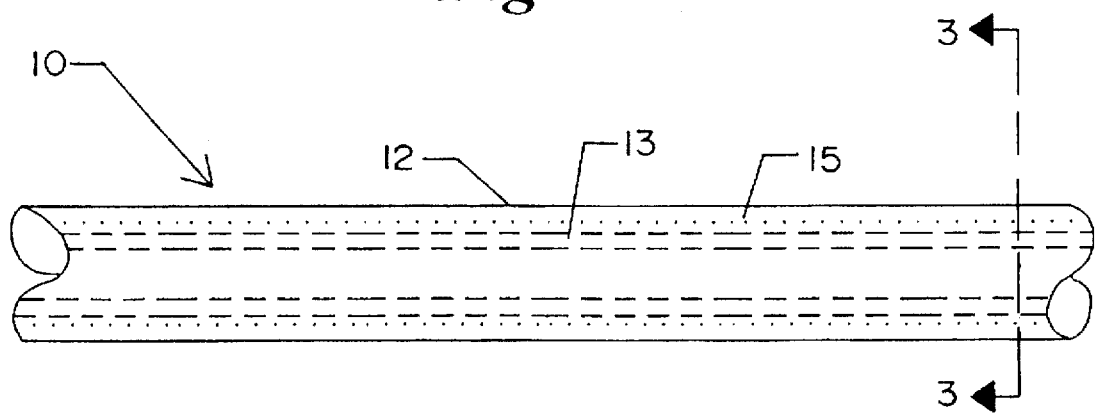
FIG. 1 is a plan view showing a portion of the thin-walled catheter of this invention.

FIG. 1 shows a thin-walled guide catheter 10. Catheter 10 comprises an outer tubular member 12 which surrounds and is coaxial with an inner tubular member 13 shown in dashed phantom lines. A support member 15 is shown in dotted phantom lines. Member 15 is preferably a metal braid which also surrounds and is coaxial with member 13.

Figure 2:
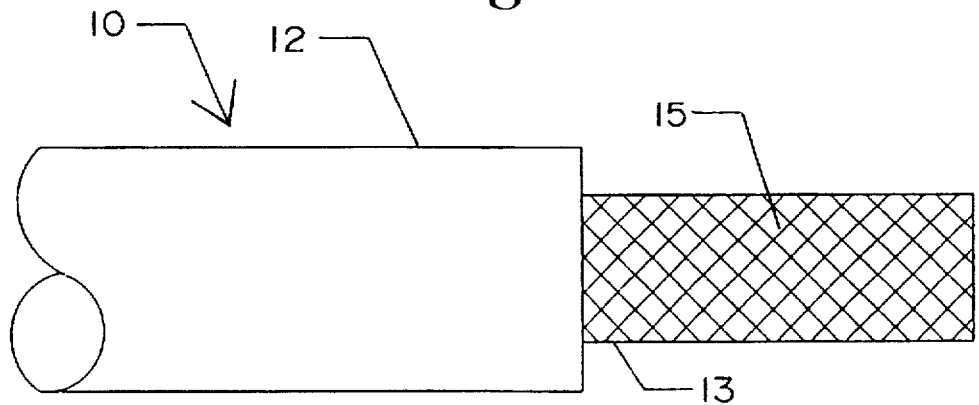
FIG. 2 is another plan view of a portion of the catheter of FIG. 1 with part of the catheter removed to show an inner construction.

FIG. 2 is a drawing of a portion of catheter 10. Member 12 is shown having a portion cut away to reveal that inner member 13 is surrounded by metal braid 15.

Figure 3:
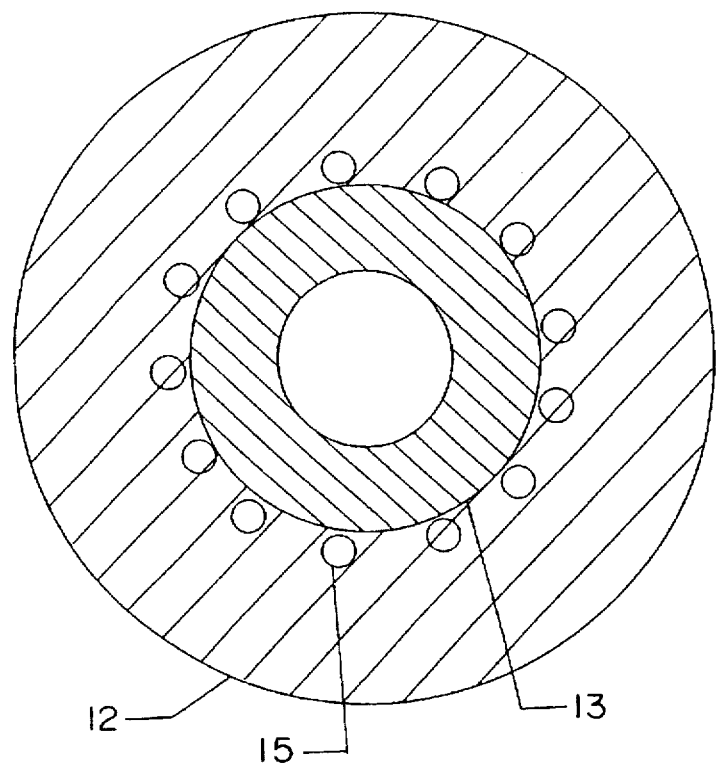
FIG. 3 is a plan view taken along section line 3—3 of FIG. 1.

FIG. 3 is a sectional plan view taken along section line 3—3 of FIG. 1. Here it can more clearly be seen that member 13 is a generally tubular member which defines a central lumen. Tubular member 12 surrounds tube 13 and is also coaxial with member 15 and the lumen it defines. Support braid 15 surrounds member 13 and is preferably imbedded in a portion of the wall of member 12.

Figure 4:
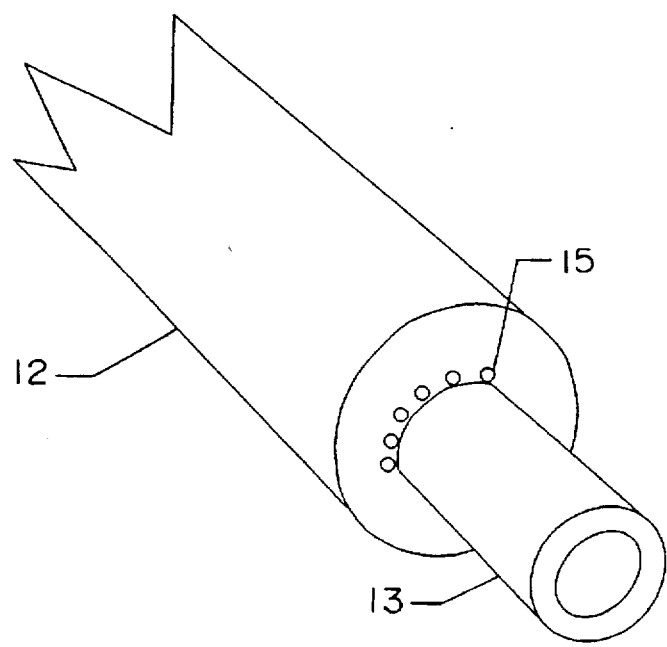
FIG. 4 is a perspective view of a portion the catheter of this invention.

FIG. 4 is a perspective view that again shows how member 13 defines a central lumen for the catheter. Member 13 is surrounded by braid 15 which is imbedded in member 12.

From a review of FIGS. 1-4 it becomes apparent that one of the limitations on lumen size is the thickness of the walls of tubular members 12 and 13. As the lumen size increases, if the walls of tubes 12 and 13 remain the same, the outside diameter of catheter 10 will increase to a point where it cannot be properly used intravascularly. To avoid this undesired increase in outside diameter, it is preferable to decrease the thickness of the walls of members 12 and 13 as the lumen diameter increases. However, prior art large lumen, thin-walled catheters are prone to kinking.

One major reason kinking increases with thin-walled catheters is that the rigidity provided by the prior art metallic support members becomes insufficient as the catheter walls become thinner. Such prior art support members are often constructed of a braid made from annealed stainless steel wire. It is well known that the annealing process will yield a comparatively low tensile strength, for example, about 140 kpsi.

Catheter failure due to kinking is caused by compressive forces that collapse the catheter wall into its lumen. The support member, or braiding wire, is used to resist the compressive force. As the catheter is put through the placement process to reach the desired placement within the body it is torqued and maneuvered such that it is forced into tighter loops and bends. As these loops and bends become tighter and tighter, the compressive forces increase until the yield strength of the support member is exceeded. When the external stress (compressive forces) exceeds the ultimate tensile strength (stress) of the braiding wire material, failure or kinking of the catheter wall occurs.

From the above definition of the failure mechanism for kinking, it becomes apparent that an increase in the tensile strength of the wire will allow higher compressive forces to be applied to the catheter wall without failure. Thus the higher tolerance for stress before failure correlates directly to thinner catheter walls and tighter bends than possible with annealed or lower tensile strength wire.

The apparatus of this invention overcomes the above kinking problem by using a tempered or hardened metal for support member 15. In the preferred embodiment member 15 is a braid using no. 304 stainless steel wire which has been hardened to have a high tensile strength in the range of 300 to 475 kpsi. Study has shown that tensile strengths down to 200 kpsi also offer advantageous kink resistance over the annealed braid.

The following chart illustrates the typical lumen sizes obtainable for various catheter french sizes, based on the tensile strength of the support braid wire:

| FRENCH SIZE | ANNEALED BRAID-I.D. | HIGH TENSILE BRAID-I.D. |
|---|---|---|
| 6F | 0.060 inches | 0.064 inches |
| 7F | 0.072 inches | 0.076 inches |
| 8F | 0.080 inches | 0.084 inches |
| 9F | 0.092 inches | 0.096 inches |

From the above chart the advantage of the tempered or high tensile strength braid can be clearly seen. In all french sizes shown, the high tensile braid allows a larger lumen (thinner wall) than does the prior art or annealed braid.

Figure 5:
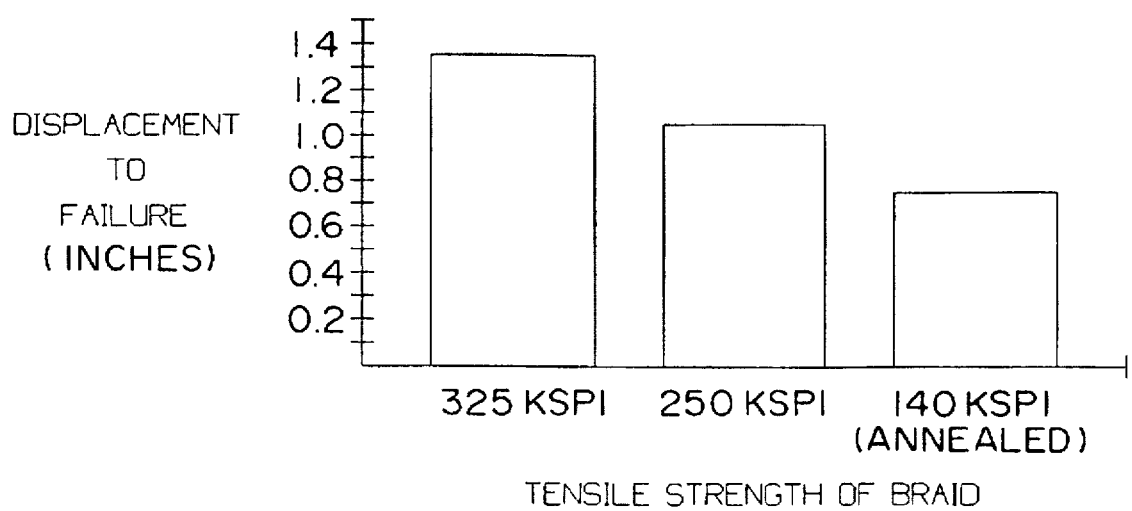
FIG. 5 is a bar graph depicting catheter kink resistance at various tensile strengths of the support braid of the catheter of this invention.

Reference is made to FIG. 5 where the bar graph also clearly depicts the advantage of the present invention with regard to kink performance. Here it can clearly be seen that the preferred embodiment of the present invention (325 kpsi braid wire) offers far greater kink performance or displacement-to-failure than does the prior art annealed version (140 kpsi braid wire). It can also be seen that an even lower tempered tensile strength of 250 kpsi braid wire still offers significantly improved kink performance over the annealed braid wire.

Finally, it has also been found that certain braid construction features are preferred for this invention. The preferred diameter of the braid wire is 0.002 inches, though diameters in the range of 0.00075 to 0.0035 are also acceptable dependent on the catheter wall dimensions. The preferred braiding density is 40 pic, though other pic densities have also been found to be advantageous.

A variation (not shown in the drawings) of the preferred embodiment of FIGS. 1-4 would be to use a single elongated generally tubular member such as 13 to define the entire catheter 10, with the support member 15 being embedded within the member 13. Thus both the inside and outside diameters of the catheter 10 would be defined by the single elongated member 13.

Having thus described the preferred embodiments of the present invention, those of skill in the art will readily appreciate the other useful embodiments within the scope of the claims hereto attached.

We claim:

1. Flexible catheter apparatus comprising:

a. a first elongated member having a first wall defining a lumen;

b. a second elongated member having a second wall and surrounding said first member; and c. one or more interwoven metallic helical strands comprising a hardened stainless steel support member situated between said first and second members for providing rigidity to said catheter, said hardened stainless steel support member being embedded in said second elongated member.

2. In a flexible catheter having a first thin-walled generally tubular member defining and coaxial with a lumen, a second thin-walled generally tubular member surrounding said first member and also coaxial with said lumen, and a support member located between said first and second members and further coaxial with said lumen, the improvement comprising:

a. said support member comprising a plurality of hardened stainless steel metallic strands braided in a helical manner around said first tubular member wherein said plurality of hardened stainless steel metallic strands are embedded in the second tubular member, and;

b. said support member having a tensile strength sufficient to prevent kinking of said flexible catheter throughout a predetermined range of flexing as the thickness of said first or second tubular member is decreased.

* * * * *